United States Patent
Vartiainen

(10) Patent No.: US 9,539,151 B2
(45) Date of Patent: Jan. 10, 2017

(54) MALE ABSORBENT ARTICLE WITH POUCH FOR HOUSING MALE GENITALS

(75) Inventor: Kent Vartiainen, Lerum (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 442 days.

(21) Appl. No.: 13/880,655

(22) PCT Filed: Nov. 11, 2010

(86) PCT No.: PCT/SE2010/051241
§ 371 (c)(1),
(2), (4) Date: Apr. 19, 2013

(87) PCT Pub. No.: WO2012/064243
PCT Pub. Date: May 18, 2012

(65) Prior Publication Data
US 2013/0218118 A1    Aug. 22, 2013

(51) Int. Cl.
A61F 13/15 (2006.01)
A61F 13/20 (2006.01)
A61F 13/471 (2006.01)
A61F 13/49 (2006.01)
A61F 13/491 (2006.01)

(52) U.S. Cl.
CPC .............. *A61F 13/471* (2013.01); *A61F 13/49* (2013.01); *A61F 13/4915* (2013.01)

(58) Field of Classification Search
USPC .................. 604/327, 346, 347, 349
See application file for complete search history.

(56) References Cited

U.S. PATENT DOCUMENTS

| 4,453,938 A | 6/1984 | Brendling |
| 4,627,846 A | 12/1986 | Ternström |
| 4,695,279 A * | 9/1987 | Steer ............................ 604/397 |
| 4,772,280 A | 9/1988 | Rooyakkers |
| 6,059,762 A | 5/2000 | Boyer et al. |

(Continued)

FOREIGN PATENT DOCUMENTS

| CN | 101065087 A | 10/2007 |
| FR | 2 701 389 A1 | 8/1994 |

(Continued)

OTHER PUBLICATIONS

Office Action (Decision on Grant) issued on Jul. 4, 2014, by the Russian Patent Office in corresponding Russian Patent Application No. 2013126694/12 (039598) and an English Translation of the Office Action (7 pages).

(Continued)

*Primary Examiner* — Michele M Kidwell
(74) *Attorney, Agent, or Firm* — Buchanan Ingersoll & Rooney PC

(57) ABSTRACT

A male absorbent article includes a liquid impermeable pouch for housing the male genitals of a user. The pouch includes an opening for inserting the male genitals into the pouch. The absorbent article includes an absorbent body positioned in the absorbent article for fluid communication with the interior space of the pouch. An inner sheet structure comprises the opening for inserting the male genitals into the pouch and is tapered and positioned between and extending from first and second upper ends in a direction towards a lower end.

15 Claims, 8 Drawing Sheets

(56) References Cited

U.S. PATENT DOCUMENTS

| | | | |
|---|---|---|---|
| 6,289,520 B1* | 9/2001 | Page | 2/403 |
| 7,104,976 B1* | 9/2006 | Allen, Sr. | 604/385.03 |
| 7,676,853 B1 | 3/2010 | Cutlip | |
| 7,799,007 B2* | 9/2010 | Hermansson et al. | 604/394 |
| 7,993,318 B2 | 8/2011 | Olsson et al. | |
| 8,475,426 B2 | 7/2013 | Helmfridsson et al. | |
| 8,926,578 B2* | 1/2015 | Drevik | 604/385.01 |
| 9,451,794 B2* | 9/2016 | Lin | A41B 9/023 |
| 2007/0073252 A1* | 3/2007 | Forgrave | 604/349 |
| 2007/0106240 A1* | 5/2007 | Nakajima et al. | 604/385.19 |
| 2007/0277285 A1* | 12/2007 | Gravette et al. | 2/78.1 |
| 2008/0178369 A1* | 7/2008 | Kitsch et al. | 2/405 |
| 2009/0182297 A1* | 7/2009 | Hedstrom et al. | 604/385.13 |
| 2013/0090621 A1* | 4/2013 | Delattre | A61F 13/471 604/385.01 |

FOREIGN PATENT DOCUMENTS

| | | |
|---|---|---|
| FR | 2 885 492 A1 | 11/2006 |
| GB | 2 142 243 A | 1/1985 |
| RU | 31507 U1 | 8/2003 |
| RU | 2 371 157 C2 | 10/2009 |
| WO | WO 85/03428 A1 | 8/1985 |
| WO | 98/29061 A1 | 7/1998 |
| WO | WO 98/29073 A1 | 7/1998 |
| WO | 99/33422 A1 | 7/1999 |
| WO | 2006/062444 A1 | 6/2006 |
| WO | 2006/123973 A1 | 11/2006 |
| WO | WO 2009/147458 A1 | 12/2009 |
| WO | WO 2010/128947 A1 | 11/2010 |

OTHER PUBLICATIONS

Office Action (Notification of the First Office Action) issued on May 28, 2014, by the State Intellectual Property Office (SIPO) of the People's Republic of China in corresponding Chinese Patent Application No. 201080070081.2, and an English Translation of the Office Action (10 pages).

International Search Report (PCT/ISA/210) issued on Jul. 11, 2011, by the Swedish Patent Office as the International Searching Authority for International Application No. PCT/SE2010/051241.

Written Opinion (PCT/ISA/237) issued on Jul. 11, 2011, by the Swedish Patent Office as the International Searching Authority for International Application No. PCT/SE2010/051241.

International Preliminary Report on Patentability (PCT/IPEA/409) issued on Jan. 30, 2013, by the European Patent Office as the International Searching Authority for International Application No. PCT/SE2010/051241.

Extended European Search Report dated Mar. 17, 2014 issued by the European Patent Office in corresponding European Patent Application No. 10859610.7 (4 pages).

* cited by examiner

MALE ABSORBENT ARTICLE WITH POUCH FOR HOUSING MALE GENITALS

TECHNICAL FIELD

The invention relates to a male absorbent article comprising a pouch for housing the male genital.

BACKGROUND ART

Male absorbent articles are known in prior art for absorbing leaking urine. For adults the leaking urine may be an effect of a disease or the adult may be so old that he is bed ridden. The external male genital organ comprises the penis and scrotum and a problem with absorbent articles for men is that the penis moves when the user changes position. Hence, the absorbent article may be working well when the penis is positioned in the middle of the article, but will function poorly when the penis is positioned in the vicinity of the side edge of the article since most of the absorbent material is positioned in the middle of the article and any abundance of urine at the side edge will most likely cause side leakage.

WO 98/48753 teaches an absorbent article comprising an inner sheet structure connected to an outer sheet structure forming an internal space into which the penis is supposed to be positioned via an opening in the inner sheet structure. The internal space is liquid impermeable and thus hinders any urine from leaking over the side edges. One problem with the solution presented in WO 98/48753 is that the penis has to be positioned in the opening by the hand of a user or by the hand of a care taker. This manipulation of the penis may be considered unhygienic and awkward.

SUMMARY

There is a need for an improved male absorbent article where the problems with prior art is rectified.

The present disclosure intends to solve the problem by providing an absorbent article comprising a liquid impermeable pouch into which a male user's penis may be inserted, and dependent on the size of the pouch also the scrotum, without the use of the hand(s) or at least with a minimum use of the hand(s).

The male absorbent article comprises an outer sheet structure defining the male absorbent article. In use the absorbent article is in the form of an undergarment comprising leg openings and a waist opening. The absorbent article comprises a liquid impermeable pouch for housing the male genitals (penis or penis and scrotum) of a user, hence the inner sheet structure and at least that part of the outer sheet structure that is part of the pouch is liquid impervious. The pouch is delimited by an inner sheet structure and the outer sheet structure and the inner sheet structure comprises an opening for inserting male genitals into the pouch. The absorbent article comprises an absorbent body positioned in the absorbent article for fluid communication with the interior of the pouch.

The present disclosure is characterized in that the inner sheet structure is delimited by: a first upper end and a second upper end; and a lower end opposite the first- and second upper ends; and a first side and a second side positioned opposite each other, wherein the first side has an extension from the lower end to the first upper end and wherein the second side has an extension from the lower end to the second upper end, and the opening being tapered and positioned between and extending from the first and second upper ends in a direction towards the lower end.

One advantage of the present disclosure lies in that the tapered opening has an upper width being wider than a lower width for allowing the male genitals to enter the pouch in the upper width when putting the absorbent article on and then allowing the male genitals to slide along the slit until the lower width of the slit ensures that the inner sheet structure tightens against at least a lower part and sides of the male genitals and thereby securing at least the penis within the pouch. The tapered opening thus allows for minimum use of hands for positioning the penis or penis and scrotum in the pouch.

Another advantage is that the pouch hinders side leakage and also hinders mixing of faeces and urine which limits the risk of dermatitis. The pouch thus allows for a separate construction and/or absorbent for handling faeces only.

Yet another advantage is that the pouch can hold and retain urine not yet having been absorbed by the absorbent body. Hence, the material outside the pouch and absorbent body, i.e. those parts of the absorbent article that make up the rest of the absorbent article, can be made extremely breathable since there is less risk of urine leaking to those areas of the absorbent article.

The absorbent body could be positioned completely within the pouch and between the inner sheet structure and the outer sheet structure. The absorbent body could also be positioned partly within the pouch and partly between the inner sheet structure and the outer sheet structure, wherein the absorbent body is positioned partly outside the pouch, i.e. outside the inner sheet structure, and in fluid communication with the interior space of the pouch. The absorbent body could also be positioned completely outside the pouch, wherein the absorbent body is in fluid communication with the interior space of the pouch. Hence, the pouch may comprise one or several second openings in connection to the lower end for allowing the urine in the pouch to flow to that part of the absorbent body or to the absorbent body positioned outside the pouch, via the second opening(s).

In one example of the present disclosure, the absorbent body comprises super absorbents, which gives the benefit of a thin absorbent body with high absorbent capacity.

The inner sheet structure may comprise elastic means for forming the opening and/or the pouch. The benefit of having elastic means is that the opening may be enlarged by stretching the elastic means when inserting the male genitals. Another advantage is that the elastic means adapts and tightens at least a part of the opening sides against the male genitals due to the stretching possibilities and retraction forces from the elastic means. The inner sheet structure may be in the form of an elastic material per se, or at least a part of the inner sheet structure may be in the form of an elastic material. The inner sheet structure may also comprise elastic threads attached to and/or embedded in the inner sheet structure. The inner sheet structure may comprise one or more layers. The inner sheet structure may comprise a layer made from a material that gives a soft feel to the user.

The outer sheet structure may also comprise elastic threads attached to and/or embedded in the outer sheet structure for shaping the absorbent article. For example, the elastic means may help forming side leakage barriers, i.e. so called standing gathers, in the outer sheet structure. The outer sheet structure may comprise one or more layers. The outer sheet structure may comprise a layer made from a material that gives a soft feel to the user.

The inner sheet structure is directly or indirectly attached to the outer sheet structure via the first- and second upper ends, the lower end and the first- and second sides. Here "indirectly" refers to the situation where an intermediate structure is positioned between the outer sheet structure and the inner sheet structure and where the inner sheet structure is, at least partly, attached or in direct contact with the intermediate structure which in turn is, at least partly, attached or in direct contact with the outer sheet structure. For example, as been described above, the absorbent body could be the intermediate structure if positioned partly within the pouch and partly outside the pouch. Here, the absorbent body is positioned between the inner sheet structure and the outer sheet structure, wherein the absorbent body is positioned partly inside the pouch and partly outside the pouch. Here, the inner sheet structure is at least partly attached to the absorbent body and the absorbent body is attached to the outer sheet structure.

The inner sheet structure is directly or indirectly attached to the outer sheet structure along the first and second upper sides and is directly or indirectly attached to the outer sheet structure along the lower end in order to form the pouch. The inner sheet could also be directly or indirectly attached to the outer sheet structure along the first and second upper ends. One advantage with not attaching the first and second upper ends to the outer sheet structure is that the user may grab the first and second upper ends with the hands and may widen the opening by pulling the first and second upper ends apart. This advantage is however also won if the first and second upper ends are attached to the outer sheet structure since the user may stick thumbs or fingers into the opening of the pouch in connection to the first and second upper ends and may then widen the opening by pulling the first and second upper ends apart. The pouch could comprise a fastening means positioned in connection to the first and second upper ends for securing the first upper end to the second upper end above the male genitals when the male genitals are positioned in the pouch and the absorbent article is put on for use. The fastening means could be in the form of a strip of material fastened removably or non-removably attached to the first upper end and removably or non-removably attachable to the second upper end. The fastening means and/or the first and second upper ends may comprise suitable attachment means, for example, glue, mechanical fasteners such as hook-and-loop material, or any other suitable attachment means.

The inner sheet structure may be attached to the outer sheet structure by welding, glueing, or any other suitable means for attachment.

In order to facilitate the description of the present disclosure, the male absorbent article may be described as comprising an outer sheet structure comprising a front panel, a back panel and a crotch panel therebetween. In use the absorbent article comprises a first side panel extending between the front panel and the back panel on one side of the article and a corresponding second side panel extending between the front panel and the back panel on an opposite side of the article with reference to the first side panel. In use a front portion of the front panel, a back portion of the back panel, the first side panel and the second side panel forms a belt portion defining the waist opening of the absorbent article. In use the side panels, the front panel, the back, panel and the crotch panel form the leg openings.

With reference to the "imaginary" panels, the first upper end and the second upper end are positioned in the front panel; and the opening is tapered and positioned between and extending from the first- and second upper ends in a direction from the front panel to the crotch panel.

The division of the absorbent article into panels and portions is intended to facilitate the description of the present disclosure and should not be seen as limiting the invention. In this specification the following definitions have been used: the crotch panel has an extension between the user's legs; and the front panel has an extension over at least the lower abdomen; and the back panel has an extension over or between the buttocks and at least a part of the lower back. Approximately, the crotch panel constitutes 30-60% of the absorbent article and the front panel and back panel constitutes 10-40% of the absorbent article.

The extension of the various panels may differ in size dependent on design, choice of material and intended user, etc. and it is therefore not suitable to give exact measurements for the panels. In use, the side panels tie together the front panel and back panel in such a way that the absorbent article can be worn as an undergarment. Each side panel may comprise one elongated strip of material being fixedly attached to the front panel for attachment to the back panel during use. Each side panel may comprise one elongated strip of material being fixedly attached to the back panel for attachment to the front panel during use. Each side panel may comprise two elongated strips of material, one of them being fixedly attached to the front panel and the other one to the back panel for attachment to each other during use. Each side panel may comprise one elongated strip of material being fixedly attached to the front panel and the back panel such that the absorbent article is formed as an undergarment from before being in use. Here, "fixedly attached" means that the side panels are glued, welded, or in any other way attached to the front and/or back panel. Here, "fixedly attached" also means that the side panels may be a part of the same sheet material as the back panel and/or the front panel. Furthermore, the side panels, the front panel, the back panel, and the crotch panel may be of the same or different material. However, at least that part of the outer sheet structure constituting a part of the pouch must be liquid impervious in order to hinder urine from leaking through the outer sheet structure.

With reference to the earlier defined panels, the inner sheet structure is positioned in the front panel; or the inner sheet structure is positioned partly in the front panel and partly in the crotch panel wherein the lower end is positioned in the crotch panel.

It should be pointed out that the opening is tapered with the widest part in connection to the first- and second upper ends for guiding the male genitals within the pouch towards a narrower part of the opening, when the user puts the article on for use. The male genitals refer to the penis only or to the penis together with the scrotum depending on the size of the opening and the pouch. In both cases the tapered opening gives the advantage that the user can insert the penis, and in applicable cases the penis and scrotum, in the wider upper part when the absorbent article is partly put on for use, and when the user then finalizes the procedure for putting the absorbent article on by letting at least the front panel slide up over the lower abdomen in a direction from the toes to the head, the male genitals slide along the sides of the opening with the genitals inside the pouch with the increasingly narrowing opening forming a tightening unit against the male genital's sides.

Advantageously, the present disclosure has an extension from the first- and second upper ends to a position where the inner sheet structure tightens against at least a lower part and both sides of the penis root for securing the male genitals within the pouch when the article is in use.

BRIEF DESCRIPTION OF DRAWINGS

The invention will now be described below in association to a number of drawings where:

FIG. 7 schematically shows a side view along line VII-VII in FIG. 6, and wherein;

DETAILED DESCRIPTION

In FIGS. 1-7, the same reference numbers are used for like features.

Figure 1:
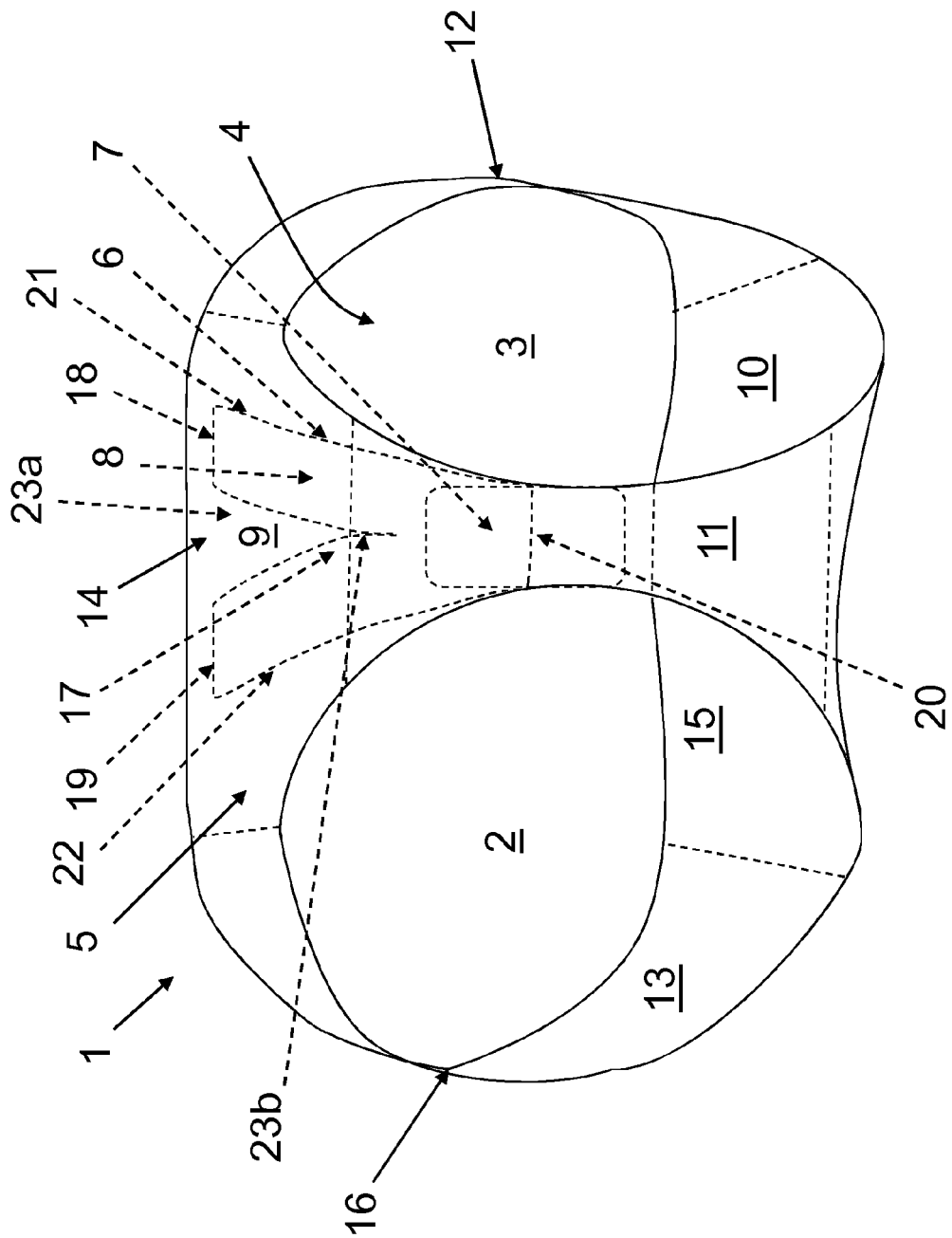
FIG. 1 schematically shows a perspective view of a male absorbent article according to a first example of the invention.

FIG. 1 schematically shows a perspective view of a male absorbent article 1 according to a first example of the invention. In FIG. 1 the absorbent article 1 is ready for use and is thus in the form of an undergarment with two leg openings 2, 3 and a waist opening 4. The absorbent article 1 comprises an outer sheet structure 5, an inner sheet structure 6 and an absorbent body 7. The inner sheet structure 6 is attached to the outer sheet structure 5 and the inner sheet structure 6 and a corresponding part of the outer sheet structure 5 form a pouch 8. In order to facilitate the description of the invention, the male absorbent article 1 is described as comprising the outer sheet structure 5 comprising a front panel 9, a back panel 10 and a crotch panel 11 therebetween. In use the absorbent article 1 comprises a first side panel 12 extending between the front panel 9 and the back panel 10 on one side of the absorbent article 1 and a corresponding second side panel 13 extending between the front panel 9 and the back panel 10 on an opposite side of the absorbent article 1 with reference to the first side panel 12. In use, a front portion 14 of the front panel 9, a back portion 15 of the back panel 10, the first side panel 12 and the second side panel 13 forms a belt portion 16. In use the first and second side panels 12, 13, the front panel 9, the back panel 10 and the crotch panel 11 form the leg openings 2, 3.

The absorbent article 1 will be further described in connection to FIGS. 2-7 where different examples are shown for creating an absorbent article 1 ready for use, i.e. with a waist opening 4 and leg openings 2, 3 as shown in FIG. 1. It should be pointed out that the description in connection to FIG. 1 is valid also for FIGS. 2-7 with regard to the pouch 8. Furthermore, in FIGS. 2-7 are shown different positions of the absorbent body 7 in relation to the pouch 8, and it should be pointed out that the below described different positions of the absorbent body 7 in relation to the pouch 8 is valid for all examples of absorbent articles 1 shown in FIGS. 1-7.

In FIG. 1 the outer sheet structure 5 is in one piece and forms an undergarment-like absorbent article 1 ready for use by putting the absorbent article on in a similar fashion as if it was an undergarment or a pair of trousers, i.e. the legs goes into the waist opening 4 and then into each of the leg openings 2, 3.

The outer sheet structure 5 may comprise one or several layers of the same or different materials with the same or different size(s). However, at least one layer in that part of the outer sheet structure 5 forming a part of the pouch 8 is liquid impermeable. The liquid impermeable material may be breathable, i.e. formed for allowing air and vapour to pass through the material. FIGS. 1-7 show that the inner sheet structure 6 and the outer sheet structure 5 each comprises one layer of material, but the inner sheet structure 6 and/or the outer sheet structure 5 could comprise several layers.

The pouch 8 is delimited by the inner sheet structure 6 and the outer sheet structure 5 and the inner sheet structure 6 comprises an opening 17 for inserting male genitals into the pouch 8.

The inner sheet structure 6 is delimited by: a first upper end 18 and a second upper end 19; and a lower end 20 opposite the first- and second upper ends 18, 19; and a first side 21 and a second side 22 positioned opposite each other. The first side 21 has an extension from the lower end 20 to the first upper end 18 and the second side 22 has an extension from the lower end 20 to the second upper end 19, and the opening 17 is tapered and positioned between and extending from the first- and second upper ends 18, 19 in a direction towards the lower end 20.

With reference to FIG. 1, the first upper end 18 and the second upper end 19 are positioned in the front panel 9; and the opening 17 is tapered and positioned between and extending from the first- and second upper ends 18, 19 in a direction from the front panel 9 to the crotch panel 11. The opening 17 is tapered with the widest part 23a in connection to the first- and second upper ends 18, 19 for guiding the male genitals within the pouch 8 towards a narrower part 23b of the opening 17, when the user puts the absorbent article 1 on for use.

In FIG. 1, the absorbent article 1 comprises an absorbent body 7 positioned partly within the pouch 8 and partly outside the pouch 8. The absorbent body 7 positioned outside the pouch 8 could be in fluid communication with the interior of the pouch 8 via the portion of the absorbent body 7 positioned inside the pouch if the pouch 8 comprises a second opening (shown in FIGS. 2-5) in the lower end 20. The second opening could comprise one or several channels between the inner sheet structure 6 and the outer sheet structure 5. However, the absorbent body 7 positioned outside the pouch 8 could be a separate absorbent body 7, for example for handling faeces. The absorbent body 7 positioned inside the pouch 8 could be a separate unit for handling urine.

In FIG. 1, the inner sheet structure 6 is directly attached to the outer sheet structure 5 along the first and second upper ends 18, 19 and the first and second sides 21, 22 and is indirectly attached to the outer sheet structure along the lower end 20 via the absorbent body 7. The first and second upper ends 18, 19 do not need to be attached to the outer sheet structure 5 but may be used as gripping flaps for widening the opening 17 when inserting the genitals in the opening 17.

Figure 2:
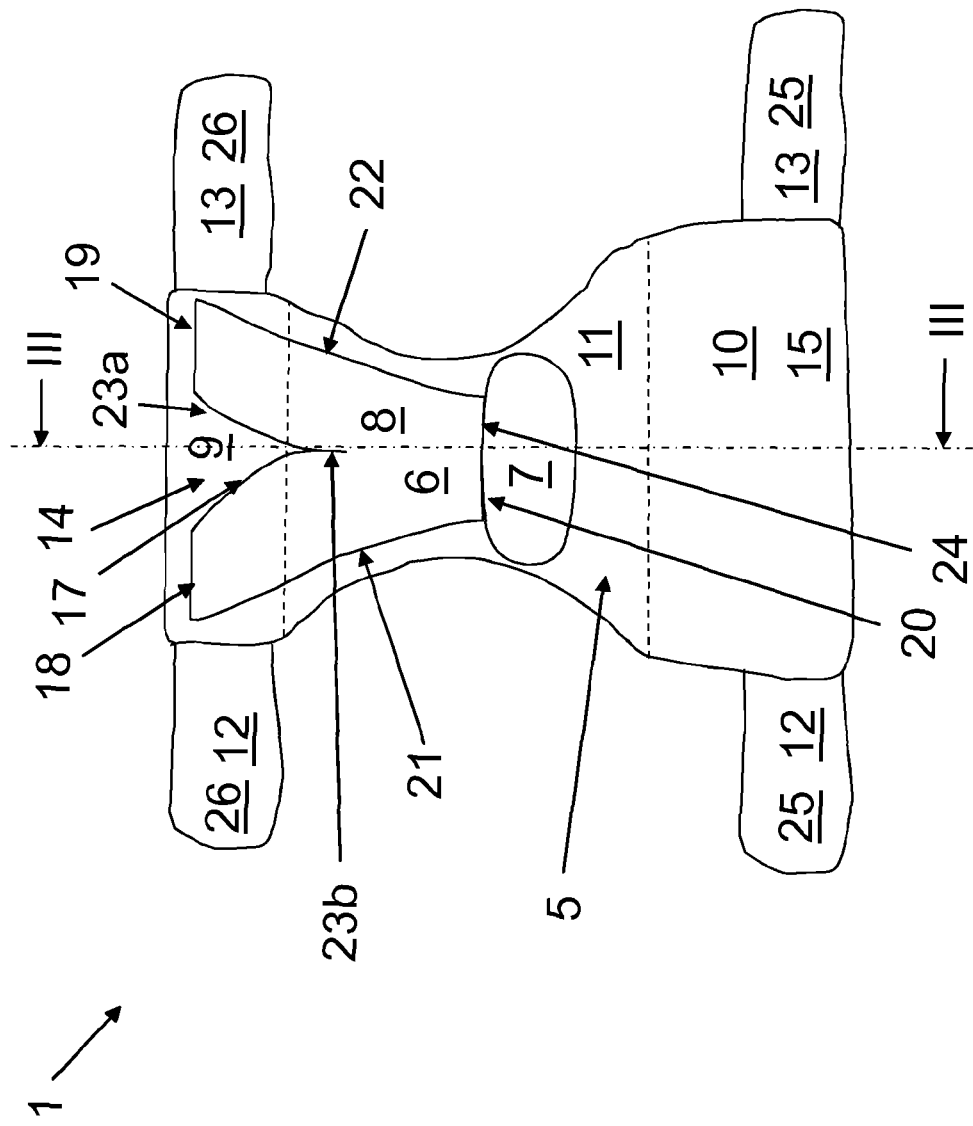
FIG. 2 schematically shows a top view of the inside of a male absorbent article in a splayed position, according to a second example of the invention.
Figure 3:
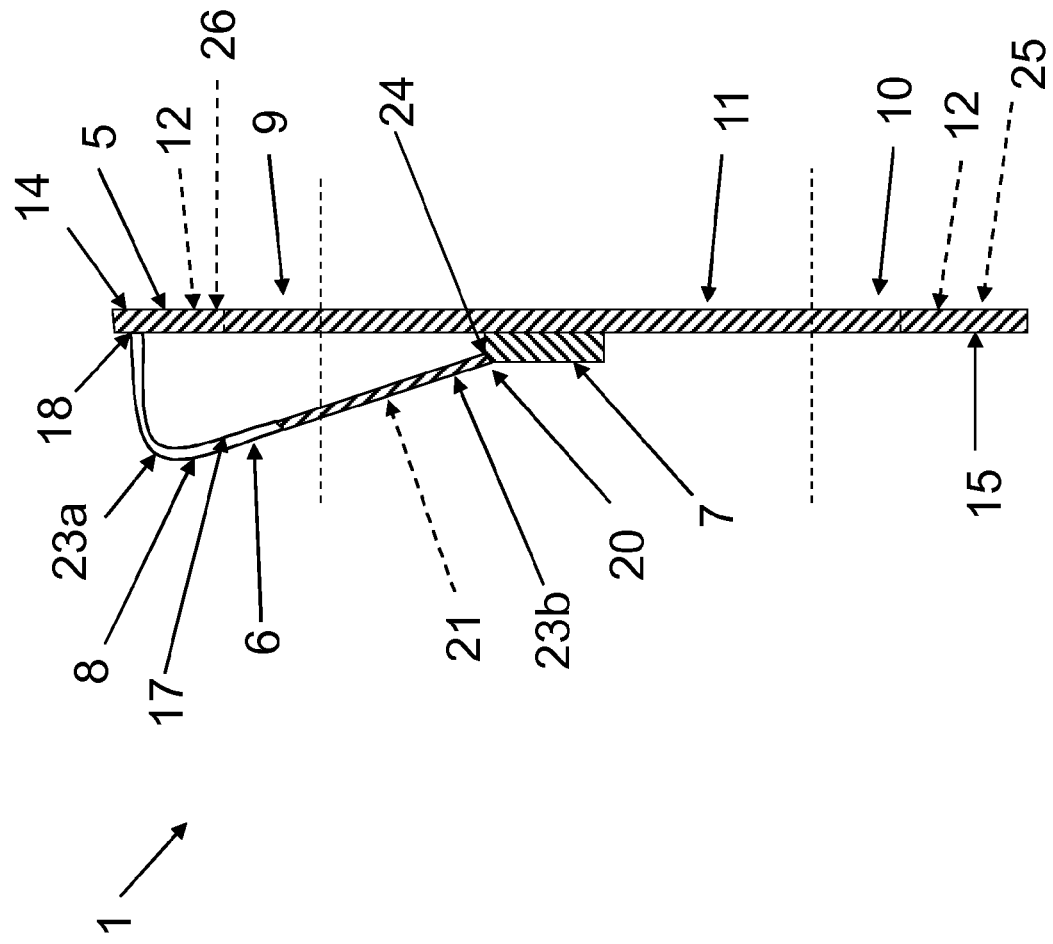
FIG. 3 schematically shows a side view along line III-III in FIG. 2.

FIG. 2 schematically shows a top view of the inside of a male absorbent article 1 in a splayed position, according to a second example of the invention, and FIG. 3 schematically shows a side view along line III-III in FIG. 2. The difference between FIG. 1 and FIG. 2 is that in FIG. 2, the entire absorbent body 7 is positioned outside the pouch 8 but in connection to the pouch 8 for liquid communication with the interior space of the pouch 8 via second opening(s) 24. Another difference is that in FIG. 2 each of the first and second side panels 12, 13 comprises two elongated strips 25, 26 of material, wherein one strip 25 is fixedly attached to the front panel 9 and the other strip 26 to the back panel 10. The elongated strips 25, 26 of material should be attached to each other during use for creating the first and second side panels 12, 13 as depicted in FIG. 1.

Figure 4:
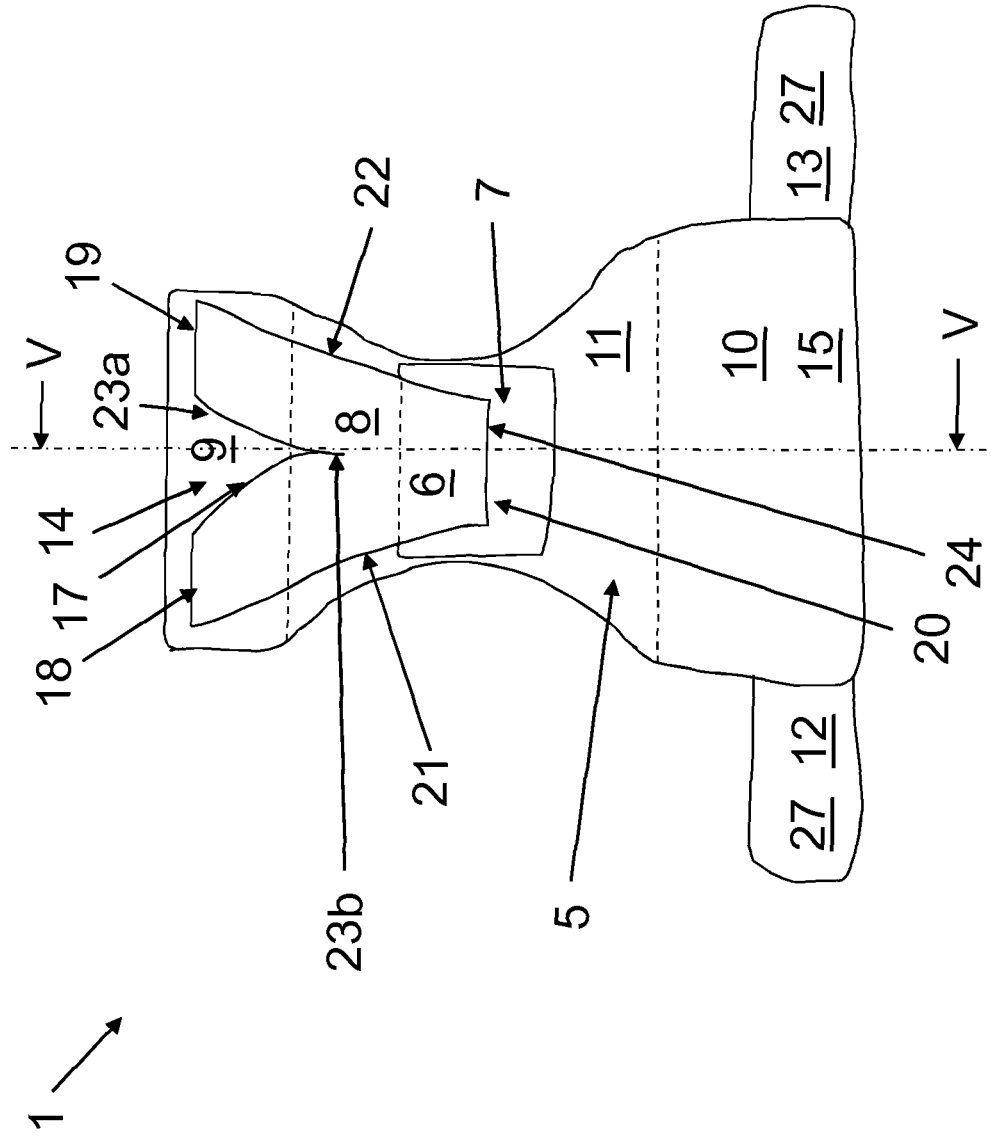
FIG. 4 schematically shows a top view of the inside of a male absorbent article in a splayed position, according to a third example of the invention.
Figure 5:
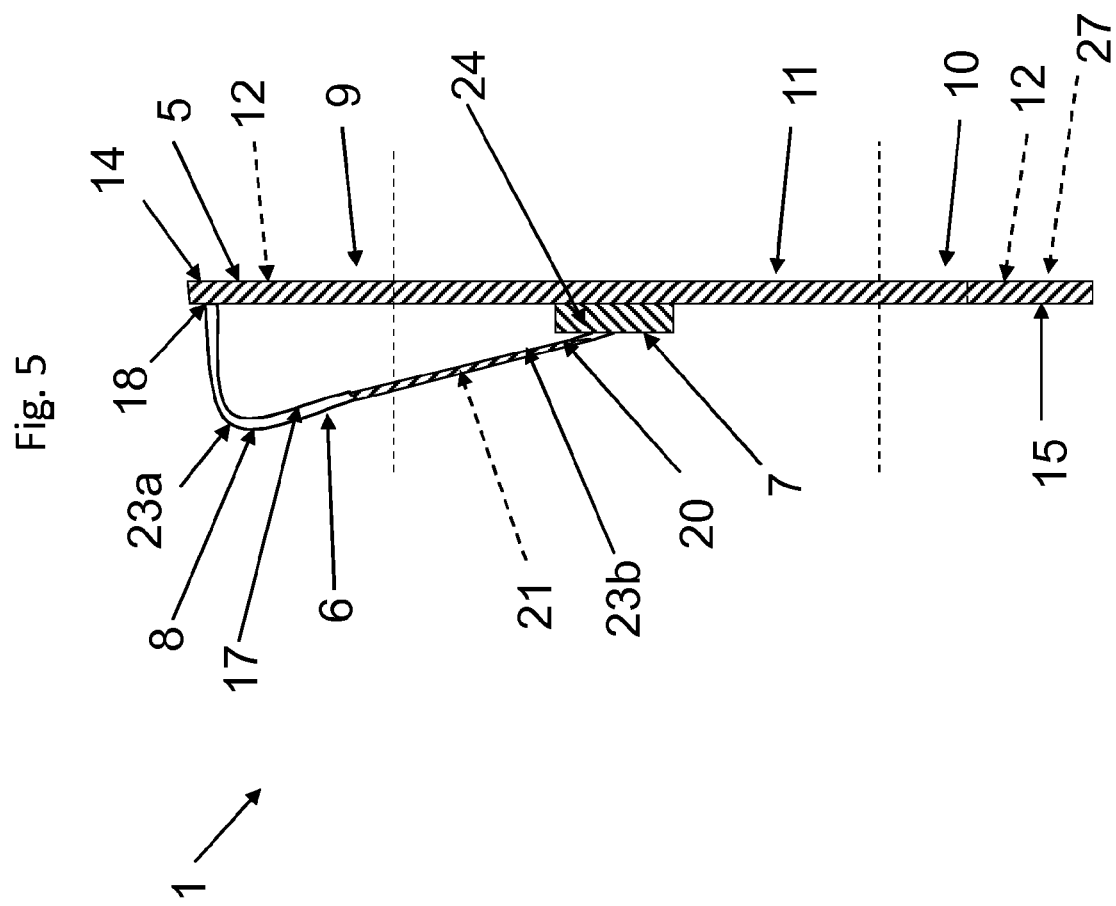
FIG. 5 schematically shows a side view along line V-V in FIG. 4.

FIG. 4 schematically shows a top view of the inside of a male absorbent article 1 in a splayed position, according to a third example of the invention, and FIG. 5 schematically shows a side view along line V-V in FIG. 4. As in FIG. 1, the absorbent body 7 is positioned outside and inside the pouch 8 but in connection to each other for liquid communication via second opening(s) 24. The second opening 24 could comprise one or several channels between the inner sheet structure 6 and the outer sheet structure 5.

FIG. 4 differs from FIG. 2 with regard to the position of the absorbent body 7. FIG. 4 differs from FIGS. 1 and 2 with regard to the first and second side panels 12, 13, but it should be pointed out that the position of the absorbent body 7 as depicted in FIG. 2 is valid also for any one of the absorbent articles 1 depicted in FIGS. 1 and 4.

In FIG. 4 each one of the first and second side panels 12, 13 comprises one elongated strip 27 of material being fixedly attached to the back panel 10 for attachment to the front panel 9 during use, by the user or somebody helping the user.

Figure 6:
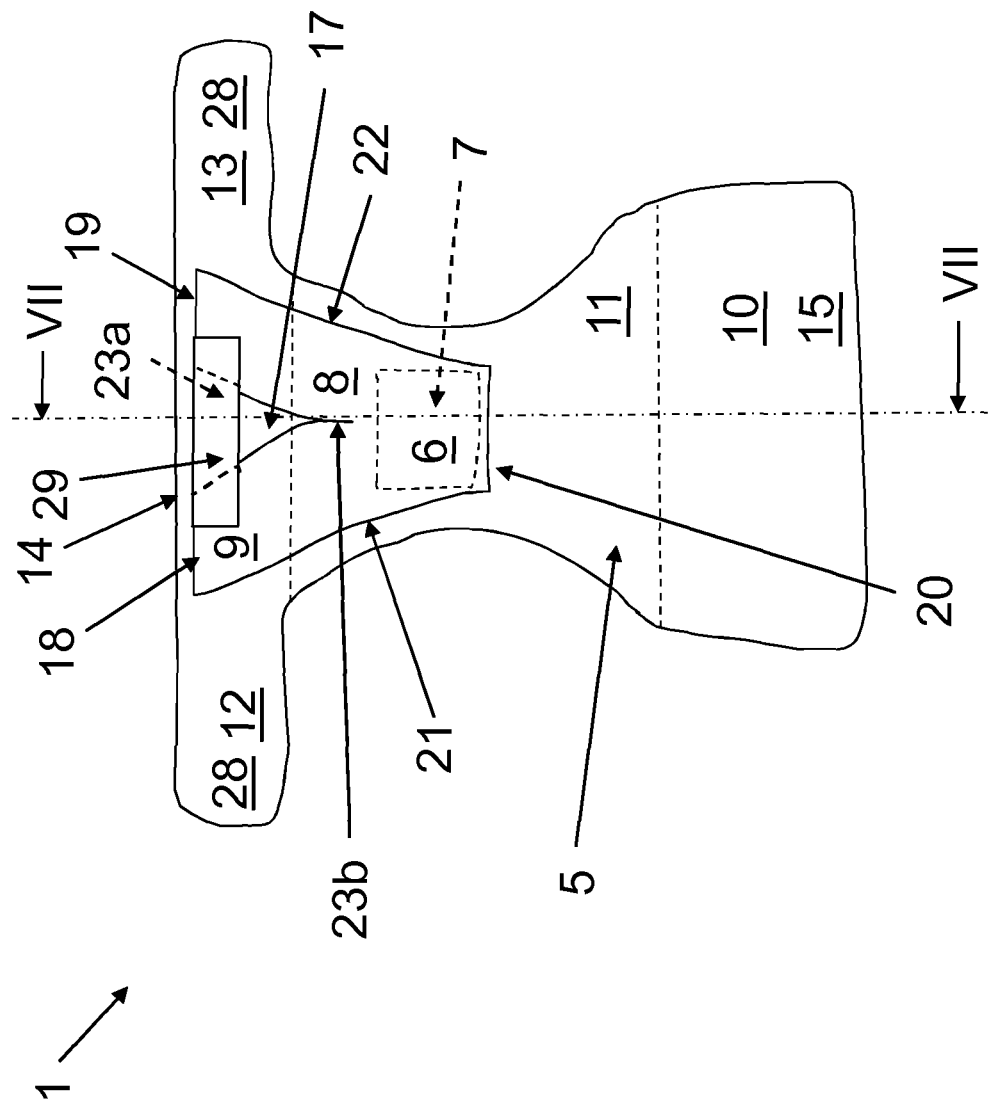
FIG. 6 schematically shows a top view of the inside of a male absorbent article in a splayed position, according to a fourth example of the invention.
Figure 7:
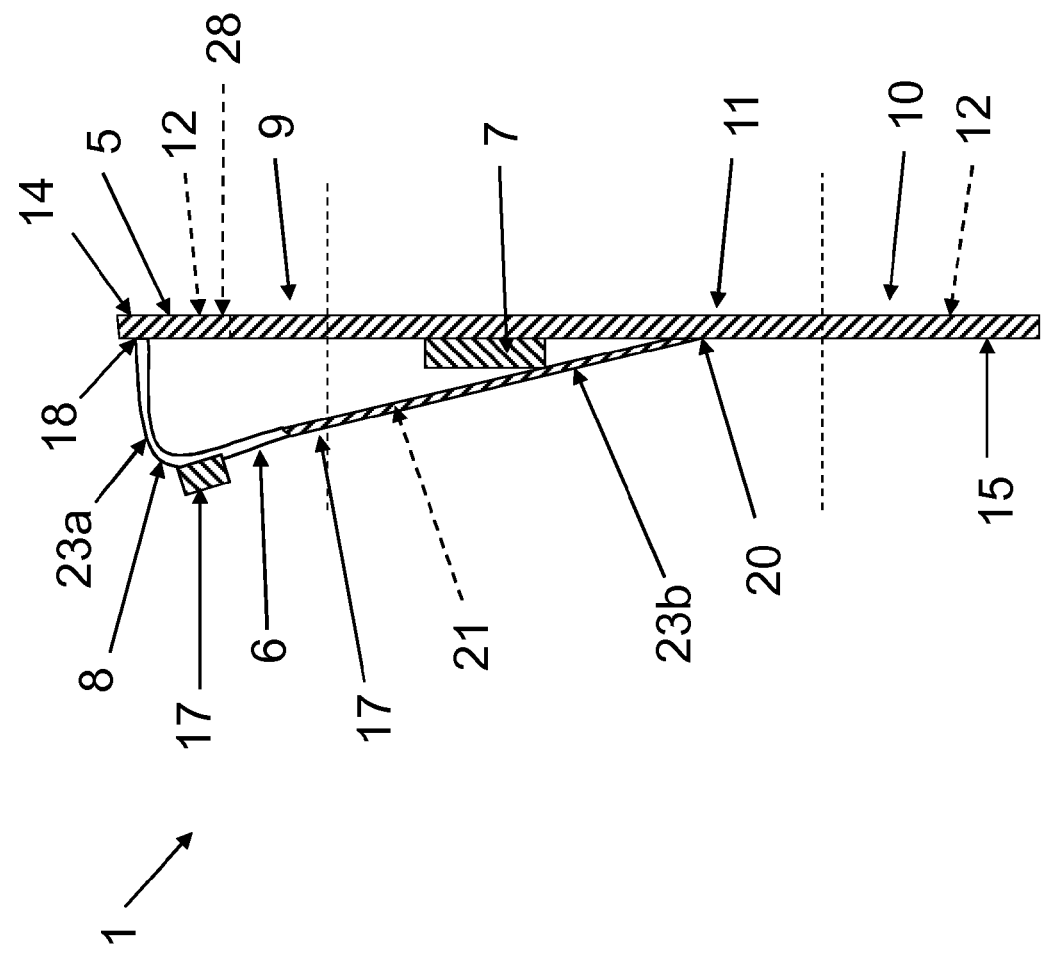

FIG. 6 schematically shows a top view of the inside of a male absorbent article 1 in a splayed position, according to a fourth example of the invention, and FIG. 7 schematically shows a side view along line VII-VII in FIG. 6.

The difference between FIG. 6 and FIGS. 1-5 is that in FIG. 6 the entire absorbent body 7 is positioned inside the pouch 8 for liquid communication with the interior space of the pouch 8.

FIG. 6 differs from FIGS. 1-5 with regard to the first and second side panels 12, 13, but it should be pointed out that the position of the absorbent body 7 as depicted in FIG. 6 is valid also for any one of the absorbent articles 1 depicted FIGS. 1-5.

In FIG. 6 each one of the side panels 12, 13 comprises one elongated strip 28 of material being fixedly attached to the front panel 9 for attachment to the back panel 10 during use, by the user or anybody helping the user.

In FIG. 6, the pouch 8 comprises a fastening means 29 positioned in connection to the first and second upper ends 18, 19 for securing the first upper end 18 to the second upper end 19 above the male genitals when the male genitals are in the pouch 8 and the absorbent article 1 is put on for use. In FIG. 6, the fastening means 29 is in the form of a strip of material fastened fixedly attached to the first upper end 18 and removably attached to the second upper end 19. In FIG. 6, the fastening means could be fixedly attached by glueing, welding, mechanical fasteners such as hook and loop or the like; or any other suitable attachment means. In FIG. 6, the fastening means 29 could be non-fixedly attached by glueing, welding, mechanical fasteners or any other suitable attachment means. Corresponding attachment means may be positioned on the outer sheet structure 5. The fastening means 29 in FIG. 6 could be used in an absorbent article according to any one of FIGS. 1-5.

Figure 8:
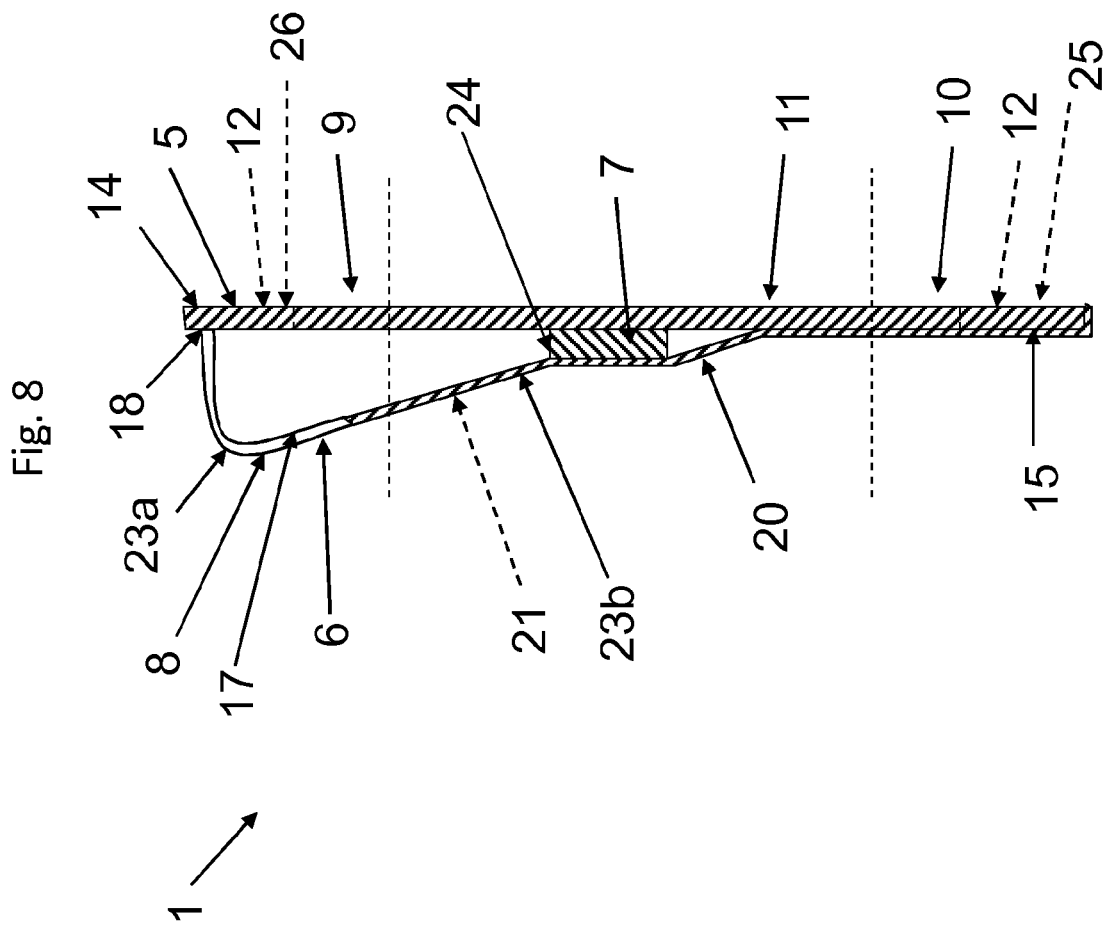
FIG. 8 schematically shows a side view along line VII-VII in FIG. 6 according to an alternative to the absorbent article in FIG. 7.

FIG. 8 schematically shows a side view along line VII-VII in FIG. 6 according to an alternative to the absorbent article in FIG. 7. In FIG. 8, the material layer constituting the inner sheet structure 6 extends further over the crotch panel 11 and the back panel 10. The possibility of utilizing the same material layer as the inner sheet structure 6 as an inner layer for parts of or the entire absorbent article is valid also for the absorbent articles described in connection to FIGS. 1-5, but the inner sheet structure 6 constituting a part of the pouch should be sealed against the outer sheet structure according to what has been described in connection to FIGS. 1-7.

With regards to the strips 25, 26, 27, 28 of material forming side panels described in connection to FIGS. 2-7, "fixedly attached" means that the first and second side panels 12, 13 are glued, welded, or in any other way attached to the front and/or back panel 9, 10. Here, "fixedly attached" also means that the first and second side panels 12, 13 may be a part of the same sheet material as the back panel 10 and/or the front panel 9. Furthermore, the first and second side panels 12, 13, the front panel 9, the back panel 10, and the crotch panel 11 may be of the same or different material. However, at least that part of the outer sheet structure 5 constituting a part of the pouch 8 must be liquid impervious in order to hinder urine from leaking through the outer sheet structure 5.

As mentioned before, the strips 25, 26, 27, 28 can be fixedly attached in one end and may comprise attachment means in the other end, by use of glue, mechanical fasteners, etc., for being attachable to the absorbent article when forming the side panels for fixing the article about the waist upon putting the article on.

The invention claimed is:

1. A male absorbent article comprising:
an outer sheet structure, the male absorbent article configured such that when the absorbent article is worn by a user, the absorbent article has leg openings and a waist opening; and
a liquid impermeable pouch for housing the male genitals of the user, the pouch delimited by an inner sheet structure and the outer sheet structure, the inner sheet structure comprising an opening for inserting male genitals into the pouch, and the absorbent article comprising an absorbent body positioned in the absorbent article for fluid communication with an interior space of the pouch,
wherein the inner sheet structure is delimited by:
a first upper end and a second upper end;
a lower end opposite the first and second upper ends; and
a first side and a second side positioned opposite each other,
wherein the first side has an extension from the lower end to the first upper end and wherein the second side has an extension from the lower end to the second upper end, and
the opening for inserting male genitals into the pouch being tapered and positioned between and extending from the first and second upper ends in a direction towards the lower end, the male genitals being at least one of the penis and scrotum,
wherein the outer sheet structure comprises a front panel, a back panel and a crotch panel between the front panel and the back panel, the absorbent article configured such that when the absorbent article is worn by the user, the absorbent article comprises a first side panel extending between the front panel and the back panel on one side of the absorbent article and a corresponding second side panel extending between the front panel and the back panel on an opposite side of the absorbent article, wherein a front portion of the front panel, a back portion of the back panel, the first side panel and the second side panel form a belt portion, the first upper end and the second upper end are positioned in the front panel; and the opening for inserting male genitals into the pouch being tapered and positioned between and extending from the first and second upper ends in a direction from the front panel to the crotch panel.

2. A male absorbent article according to claim 1, wherein the absorbent body is positioned between the inner sheet structure and the outer sheet structure.

3. A male absorbent article according to claim 1, wherein the absorbent body is positioned at least partly outside the inner sheet structure.

4. A male absorbent article according to claim 1, wherein the absorbent body comprises super absorbents.

5. A male absorbent article according to claim 1, wherein the inner sheet structure comprises elastic means for forming the opening.

6. A male absorbent article according to claim 1, wherein the inner sheet structure comprises elastic means for forming the pouch.

7. A male absorbent article according to claim 1, wherein the inner sheet structure is directly or indirectly attached to the outer sheet structure at least along the first side, the second side and at least a part of the lower end.

8. A male absorbent article according to claim 7, wherein the inner sheet structure is directly or indirectly attached to the outer sheet structure via the first and second upper ends.

9. A male absorbent article according to claim 1, wherein the inner sheet structure is positioned in the front panel.

10. A male absorbent article according to claim 9, wherein the inner sheet structure is positioned partly in the front panel and partly in the crotch panel, and wherein the lower end is positioned in the crotch panel.

11. A male absorbent article according to claim 1, wherein the opening for inserting male genitals into the pouch is tapered with a widest part in connection to the first and second upper ends for guiding the male genitals within the pouch towards a narrower part of the opening, when the article is worn by the user.

12. A male absorbent article according to claim 1, wherein the opening or inserting male genitals into the pouch has an extension from the first and second upper ends to a position where the inner sheet structure tightens against at least a lower part and both sides of a root of the penis for securing the male genitals within the pouch when the article is worn by the user.

13. A male absorbent article according to claim 1 the male genital being the penis only.

14. A male absorbent article according to claim 1, wherein the inner sheet structure and the outer sheet structure are configured such that when the male genitals are inserted into the pouch, the male genitals are located between the inner sheet structure and the outer sheet structure.

15. A male absorbent article according to claim 1, wherein the inner sheet structure and the outer sheet structure completely surround a portion of the male genitals.

* * * * *